United States Patent
Codella et al.

(10) Patent No.: US 12,295,917 B2
(45) Date of Patent: May 13, 2025

(54) DRUG DELIVERY DEVICE HAVING CONTROLLED DELIVERY AND CONFIRMATION

(71) Applicant: International Business Machines Corporation, Armonk, NY (US)

(72) Inventors: Noel C. Codella, Yorktown Heights, NY (US); Jonathan H. Connell, II, Cortlandt-Manor, NY (US); Sharathchandra Pankanti, Darien, CT (US); Nalini K. Ratha, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 966 days.

(21) Appl. No.: 17/361,535

(22) Filed: Jun. 29, 2021

(65) Prior Publication Data
US 2021/0322273 A1   Oct. 21, 2021

Related U.S. Application Data

(63) Continuation of application No. 15/848,169, filed on Dec. 20, 2017, now Pat. No. 11,052,023.

(51) Int. Cl.
*A61J 3/07* (2006.01)
*A61B 5/00* (2006.01)
(Continued)

(52) U.S. Cl.
CPC .............. *A61J 3/07* (2013.01); *A61B 5/073* (2013.01); *A61B 5/14507* (2013.01); *A61B 5/14539* (2013.01); *A61B 5/6861* (2013.01); *A61B 5/6873* (2013.01); *A61K 9/2072* (2013.01); *A61K 9/4808* (2013.01); *G16H 10/60* (2018.01); *G16H 20/10* (2018.01); *A61B 5/07* (2013.01); *A61B 5/4833* (2013.01); *A61B 5/6885* (2013.01); *A61B 2503/08* (2013.01); *A61B 2505/07* (2013.01); *A61M 31/002* (2013.01); *G16H 10/20* (2018.01)

(58) Field of Classification Search
CPC ........ G16H 10/20; G16H 10/60; G16H 20/10; G16H 20/13; G16H 40/67; A61B 5/6873; A61B 5/6861; A61B 5/073; A61M 31/002
See application file for complete search history.

(56) References Cited

U.S. PATENT DOCUMENTS

| | | |
|---|---|---|
| 2011/0160129 A1 * | 6/2011 | Imran .................. A61K 31/155 514/11.3 |
| 2011/0231202 A1 | 9/2011 | Hanina |

(Continued)

OTHER PUBLICATIONS

Huang, Gregory, "Electroactive Polymers." https://www.technologyreview.com/s/401750/electroactive-polymers/, Dec. 1, 2002, pp. 1-6.

(Continued)

*Primary Examiner* — Chelsea E Stinson
*Assistant Examiner* — Anh Bui
(74) *Attorney, Agent, or Firm* — Kristofer Haggerty; Otterstedt & Kammer PLLC

(57) ABSTRACT

A drug delivery device includes a capsule, a logic circuit disposed within the capsule, and an actuator connected to the logic circuit and configured to expose an interior of the capsule to an exterior of the capsule upon activation by the logic circuit.

5 Claims, 6 Drawing Sheets

(51) Int. Cl.
*A61B 5/07* (2006.01)
*A61B 5/145* (2006.01)
*A61K 9/20* (2006.01)
*A61K 9/48* (2006.01)
*G16H 10/60* (2018.01)
*G16H 20/10* (2018.01)
*A61M 31/00* (2006.01)
*G16H 10/20* (2018.01)

(56) References Cited

U.S. PATENT DOCUMENTS

| | | |
|---|---|---|
| 2013/0063579 A1 | 3/2013 | Hanina |
| 2014/0184772 A1 | 7/2014 | Hanina |
| 2015/0352343 A1 | 12/2015 | Hafezi |
| 2017/0274194 A1 | 9/2017 | Robertson |
| 2018/0164221 A1 | 6/2018 | Singh et al. |
| 2019/0183732 A1 | 6/2019 | Codella et al. |

OTHER PUBLICATIONS

Tian et al., "Molecular Actuators Designed with S . . . N(sp(2)) Hemibonds Attached to a Conformationally Flexible Pivot" Chem. Mater. Apr. 2009, 21, pp. 2149-2157.
Paul J. Otterstedt, List of IBM Patents or Patent Applications Treated as Related, pp. 1-2, Jun. 29, 2021.

* cited by examiner

DRUG DELIVERY DEVICE HAVING CONTROLLED DELIVERY AND CONFIRMATION

CROSS-REFERENCE TO RELATED APPLICATIONS

This application is a continuation of U.S. patent application Ser. No. 15/848,169 filed Dec. 20, 2017, the complete disclosure of which is expressly incorporated herein by reference in its entirety for all purposes.

BACKGROUND

The present disclosure relates generally to medical devices and more particularly to a drug delivery system for controlled delivery of medication with confirmation thereof.

One challenge faced in the healthcare field takes place at home, where patients manage their own care and medication compliance. Healthcare providers often cannot know for certain if patients have faithfully taken medication at proper intervals and with the correct doses. Healthcare professionals also cannot be present to prevent accidental overdose or to ensure that the correct medication is administered.

In at least the case of medical trials, these issues take on a different importance, where drug development relies on the observation and confirmation that the medication has been correctly administered.

BRIEF SUMMARY

According to an embodiment of the present invention, a drug delivery device includes a capsule, a logic circuit disposed within the capsule, and an actuator connected to the logic circuit and configured to expose an interior of the capsule to an exterior of the capsule upon activation by the logic circuit.

According to an embodiment of the present invention, a method of controlling a drug delivery device comprising a capsule, a logic circuit disposed within the capsule, and an actuator connected to the logic circuit includes sensing a location of the drug delivery device, determining entry of the drug delivery device into an intestine using the location, communicating an authorization request to an external computer system upon determining entry into the intestine, receiving an authorization from the external computer system, and activating, by the logic circuit, the actuator to expose an interior of the capsule to an exterior of the capsule upon receipt of the authorization.

According to an embodiment of the present invention, a method of controlling a drug delivery device comprising a capsule, a logic circuit disposed within the capsule, and an actuator connected to the logic circuit includes sensing a location of the drug delivery device, determining entry of the drug delivery device into an intestine using the location, communicating an authorization request to an external computer system upon determining entry into the intestine, determining an authorization fail from the external computer system, and activating, by the logic circuit, the actuator to render a medication containing with the capsule insert upon receiving the authorization fail upon determination of the authorization fail.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide one or more of the following advantages:

accurate consumption measurement;
    controlled dosing (e.g., prevention of overdose);
    ensured proper medication administration; and
    targeted delivery of drug compounds to particular regions of digestive system.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Embodiments of the present invention relate to an oral drug delivery system that records the administration of medication to a patient, controls the delivery of the medication, and reports or logs information about the administration and release of the medication (e.g., to healthcare professionals). According to one or more embodiments of the present invention, the drug delivery system includes a drug delivery device, wherein the system determines a consumption status of the drug delivery device, and once the drug delivery device has passed the patient's stomach (and can no longer be regurgitated or vomited), controls medication delivery in adherence to a prescription, thereby preventing overdose, abuse, or delivery of incorrect medication. According to one or more embodiments of the present invention, the drug delivery device is configured to detect attempts to extract medication from the device.

Figure 1:
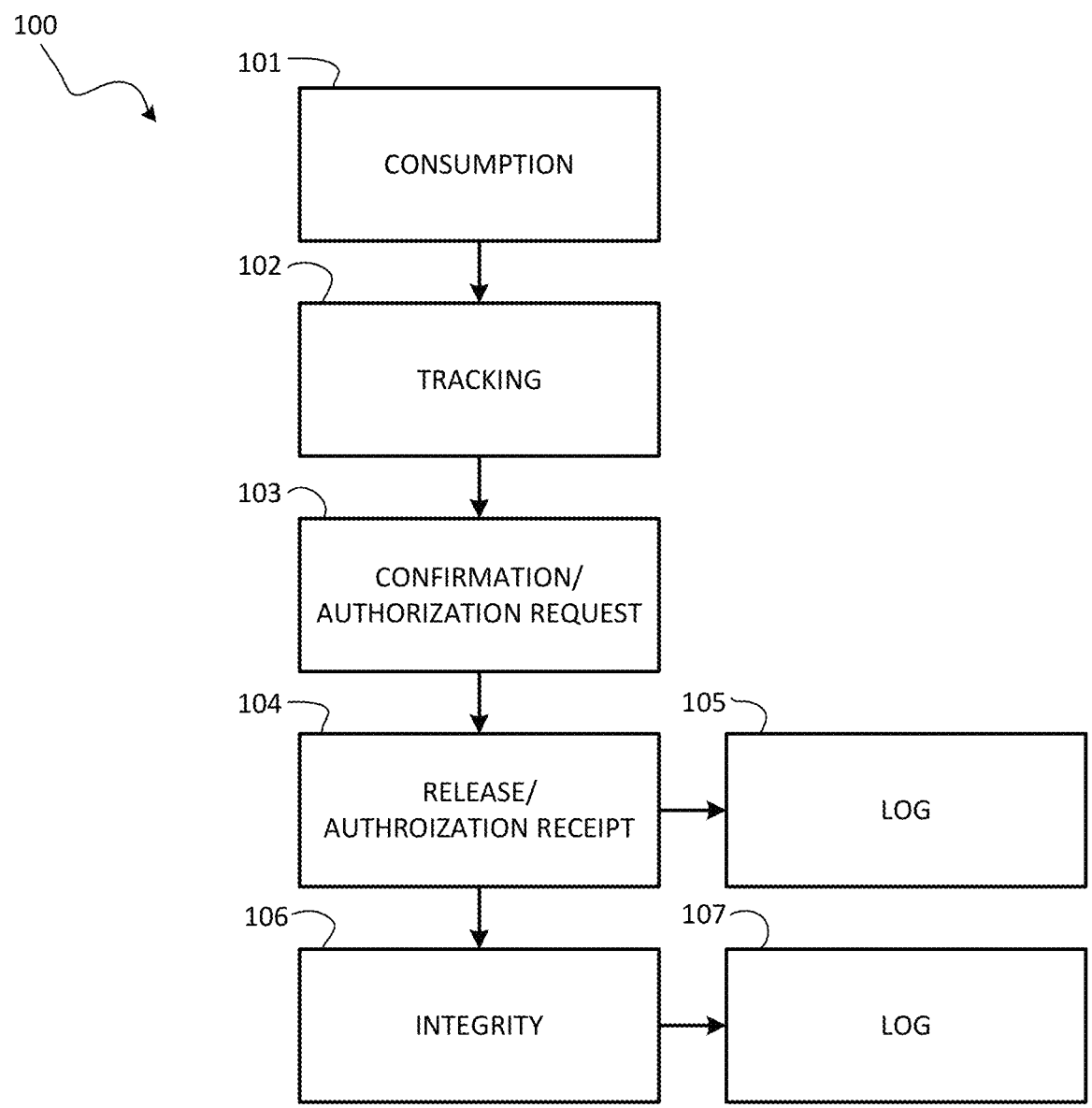
FIG. 1 is a flow diagram of a method according to an embodiment of the present invention.

Referring to FIG. 1, in a method 100 according to one or more embodiments of the present invention a patient consumes a drug delivery device 101, and a position of the drug delivery device is tracked 102 through the digestive system. Tracking can be performed using, for example, one or more built-in electrochemical sensors.

According to one or more embodiments of the present invention, the drug delivery device includes a pH sensor. Since the intraluminal pH rapidly changes from highly acidic stomach (e.g., with a pH between about 1.5 to 3.5) to about pH 6 in the duodenum, the drug delivery device can use the pH sensor to confirm passage into the small intestine 103.

According to at least one embodiment of the present invention, the pH sensor includes a measuring electrode, a reference electrode, and a temperature sensor. A signal output by the pH sensor can be processed (e.g., applied through preamplifier) and communicated to an external (to the patient) computer system for analysis, confirming a sufficient drop in pH to confirm the drug delivery device's location outside the stomach.

The drug delivery device communicates with the external computer system, confirming consumption once past stomach 103. The drug delivery device includes a wireless communication package for communicating with the external computer system. According to an exemplary embodiment of the present invention, the drug delivery device measures exogenous pH levels. The confirmation can be performed by the drug delivery device itself or by the external computer system.

According to at least one embodiment of the present invention, the drug delivery device releases 104 a medication according to prescribed dosage, timed release, and/or digestive location based release. The release is communicated to the external computer system where the release is logged 105.

According to an embodiment of the present invention, the drug delivery device can communicate with the external computer system to confirm adherence to a prescription. For example, the external computer system stores information about dosage and timing defined by a certain prescription. In a case where the patient incorrectly takes an incorrect drug delivery device, the drug delivery device will request an authorization from the external computer system (e.g., upon confirming consumption) for release of its contents. According to an embodiment of the present invention, the confirmation 103 includes an authorization request. In this case the drug delivery device is denied authorization from the external computer system when the external computer system communicates an authorization fail to the drug delivery device, and the contents are not released or are rendered inert. The request for authorization 103 from the drug delivery device can include information about the type of medication and/or dosage, which are to be confirmed by the external computer system by comparing this information with the stored prescription. Similarly, the external computer system can capture information about the number of drug delivery devices consumed, and make decisions about which, if any, devices to grant authorization to release contents.

According to an embodiment of the present invention, the electronics package can determine an authorization fail (see block 104, FIG. 1) upon the expiry of a timer (i.e., no authorization is received within a given time period) or upon an explicit communication from the external computer system in the case where the authorization request is not to be granted.

It should be understood that the external computer system can embodiment a variety of logic for comparing information received from the drug delivery device to stored information (e.g., prescriptions, drug interactions, etc.) in making authorization decisions.

One of ordinary skill in the art would recognize that the drug delivery device may contain, or may itself be, a placebo.

According to at least one embodiment of the present invention, the drug delivery device continuously monitors its own integrity 106. If the drug delivery device is disturbed, a signal indicating a breach (or possible breach) in integrity is communicated by the drug delivery device to the external computer system where the activity is logged 107. Further, in at least one embodiment of the present invention, the drug delivery device confirms release of its contents at 106, where the external computer system can log 107 a successful delivery.

Figure 2:
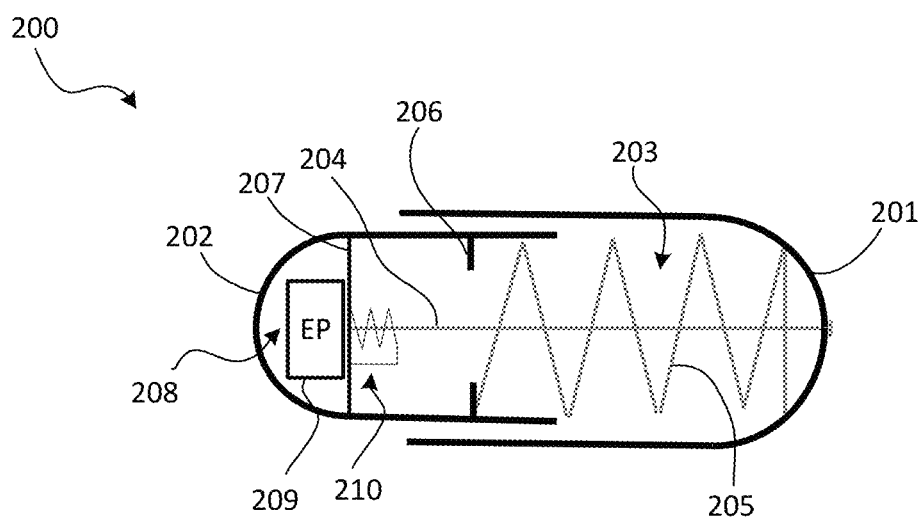
FIG. 2 is a diagram of a drug delivery device according to an embodiment of the present invention.

According to at least one embodiment of the present invention, the drug delivery device 200 (see FIG. 2) controls a release of the medication. The drug delivery device 200 comprises a capsule having a first side 201 and a second side 202. In at least one embodiment the second side 202 fits inside the first side 201, where the first and second sides have a press fit, sealing a medication 203 inside the drug delivery device 200. The drug delivery device 200 further comprises a fiber 204 (e.g., formed of a biocompatible plastic material) that secures the first and second sides 201-202 together. The drug delivery device 200 further comprises a resilient member 205 (e.g., a coil spring, torsion spring, compound spring, etc.) applying a force to the first and second sides 201-202. The resilient member 205 has a first end contacting the first side 201 and a second end contacting the second side 202. The second side 202 can comprises a structure 206 such as a ridge or lip, disposed to contact the second end of the resilient member 205. In at least one embodiment of the present invention, the second end of the resilient member 205 contacts an inner wall 207 of the second side 202 forming a compartment 208 housing an electronics package 209 (EP). The electronics package 209 can include the wireless communication package, a battery, a processor, a memory and the like. The drug delivery device 200 further comprises a heater 210. The electronics package 209 outputs an actuation signal powering the heater 210, which melts through the fiber 204 securing first and second sides 201-202 together. The heater 210 functions as an actuator. Once melted, the spring 205 causes the first and second sides 201-202 to separate, exposing the medication 203 to an exterior of the drug delivery device 200. According to at least one embodiment of the present invention, the heater 209 is disposed in the compartment 208, and is not exposed to an exterior (e.g., to human tissue).

According to at least one embodiment of the present invention, the power supply can include an electronic power supply, a kinetic power supply, a biochemical power supply and the like. For example, when power is supplied through mechanical potential energy, such as a compressed spring, miniaturization problems can be alleviated. These miniaturization problems can be a barrier to ingested devices. According to an embodiment of the present invention, when safely housed within the compartment 208, the actuation within the intestine can be triggered by a chemical sensor sensing pH in the stomach and intestine, biochemical sensors, timers, etc.

Figure 3:
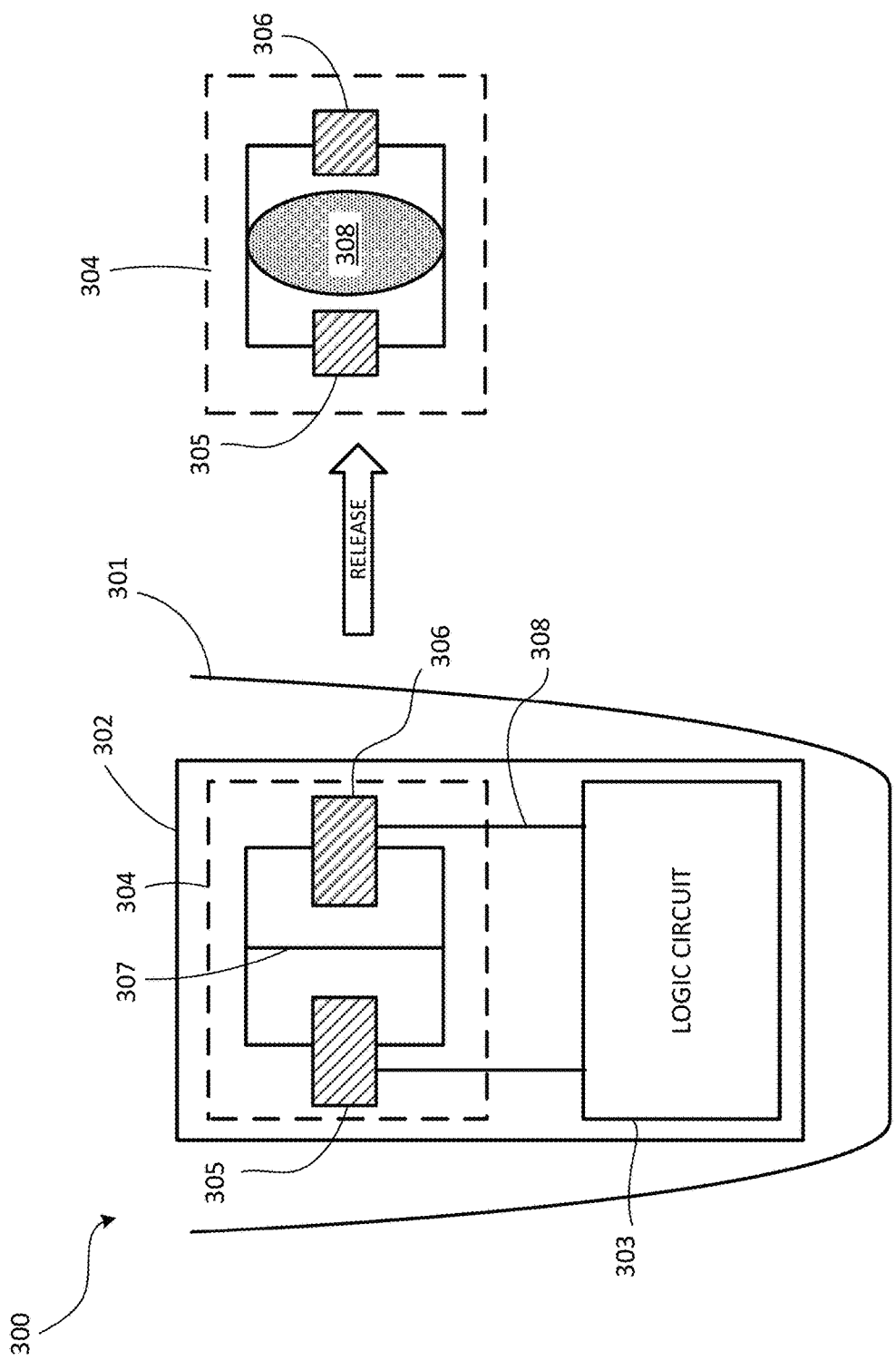
FIG. 3 is a diagram of a drug delivery device according to an embodiment of the present invention.

According to at least one embodiment of the present invention, the drug delivery device 300 (see FIG. 3) comprises a capsule 301 (or a side of the capsule). The capsule 301 contains an electronics package 302 comprising a logic circuit 303, including for example, a processor, a transmitter, and a receiver, and an actuator device 304. According to at least one embodiment of the present invention, the electronics package 302 further comprises a power supply (not shown). According to at least one embodiment of the present invention, the actuator device 304 comprises electroactive polymer actuators 305 and 306 forming a drug release mechanism. Actuators 305 and 306 are in a relaxed state. The actuator device 304 can be adhered to wall of the capsule 301. The logic circuit 303 outputs a signal to the actuators 305 and 306 via a connection 308, e.g., a conductive lead, causing a contraction in the actuators 305 and 306. The contraction in the actuators 305 and 306 causes a wall of the capsule 301 to break open, e.g., along a seam or thinned line 307 formed in the capsule, exposing the contents of the drug delivery device to an exterior through an opening 308. In FIG. 3, the actuator device 304 is shown with the opening 307 when the actuators, e.g., 308, are in a contracted state. According to at least one embodiment of the present invention, in the case of a seam, one or more actuator devices 304 break the seam, thereby forming the opening. Accordingly, a medication can be delivered to a patient.

Figure 4:
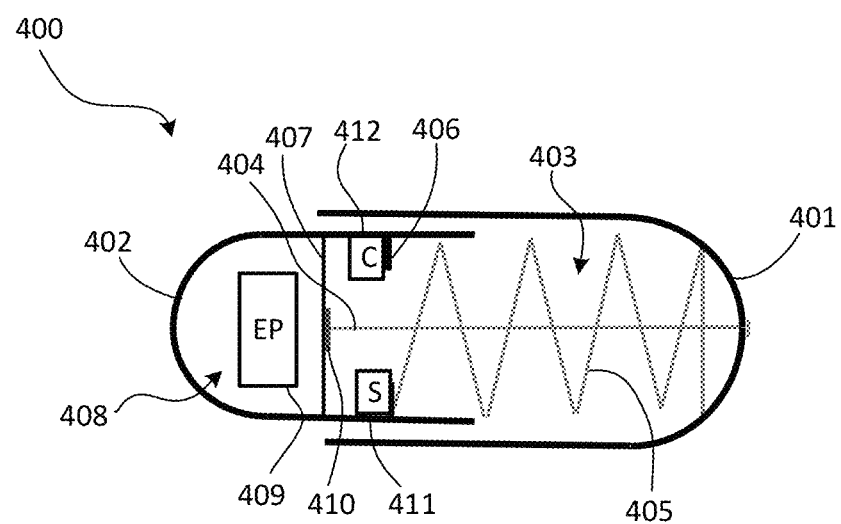
FIG. 4 is a diagram of a drug delivery device according to an embodiment of the present invention.
Figure 5:
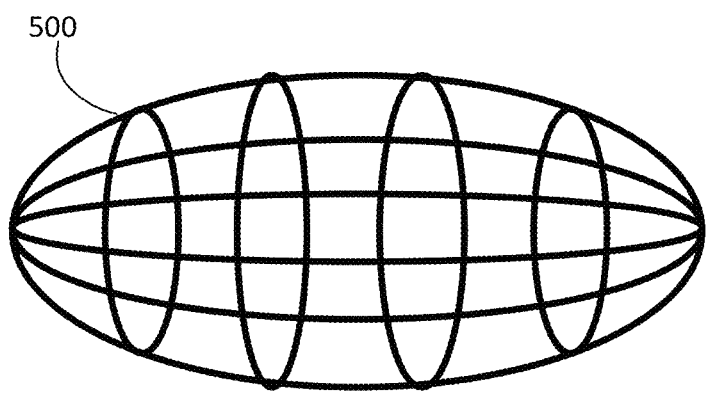
FIG. 5 is a diagram of a drug delivery device according to an embodiment of the present invention.

According to at least one embodiment of the present invention, the drug delivery device 400 (see FIG. 4) comprises a capsule having a first side 401 and a second side 402. In at least one embodiment the second side 402 fits inside the first side 401, where the first and second sides have a press fit, sealing a medication 403 inside the drug delivery device 400. The drug delivery device 400 further comprises an electroactive polymer 404 that secures the first and second sides 401-402 together. The electroactive polymer 404 functions as an actuator. The drug delivery device 400 further comprises a resilient member 405 (e.g., a coil spring, torsion spring, compound spring, etc.) applying a force to the first and second sides 401-402. The resilient member 405 has a first end contacting the first side 401 and a second end contacting the second side 402. The second side 402 comprises a structure 406 such as a ridge or lip, disposed to contact the second end of the resilient member 405. In at least one embodiment of the present invention, the second end of the resilient member 405 contacts an inner wall 407 of the second side 402 forming a compartment 408 housing an electronics package 409.

According to at least one embodiment of the present invention, the electroactive polymer 404 is activated by a voltage applied by the electronics package 409, which causes the electroactive polymer 404 to contract. According to at least one embodiment of the present invention, the resilient member 405 does not compress during contraction, as it is already fully compressed. According to at least one embodiment of the present invention, a threshold adhesion device 410 is configured to withstand a force of the resilient member 405 alone, and to break upon the contraction of the electroactive polymer 404.

According to at least one embodiment of the present invention, the electronics package 209/409 includes an accelerometer switch. The switch is sensitive to shock. A possible breach in the drug delivery device can be sensed upon breaking an acceleration sensitive filament disposed in a fuse. In this way, the fuse, including the acceleration sensitive filament can be a powerless accelerometer switch. A change in the switch's condition (upon breaking the filament) can be indicative of a possible breach in the drug delivery device.

According to at least one embodiment of the present invention, the drug delivery device can comprise a conductive cage 500. The conductive cage can be disposed in a portion of a shell of the drug delivery device. The conductive cage can be connected to the electronics package 209/409 of the drug delivery device, where the electronics package 209/409 is configured to sense a break in the conductive cage 500. According to at least one embodiment of the present invention, the cage is used to detect an intrusion into the drug delivery device. The cage can be formed from a semi-conductor material, wherein resistance between at least two vertices of the cage would change upon a break in the cage. According to at least one embodiment of the present invention, the electronics package 209/409 includes a logic circuit to detect such a disruption.

According to at least one embodiment of the present invention, the drug delivery device 400 includes a switch (S). The switch is pressure sensitive, and is configured to detect a loss of pressure applied by the resilient member 405. The switch 411 sends a signal if drug delivery device 400 is opened prior to consumption (e.g., passing the patient's stomach).

According to at least one embodiment of the present invention, the drug delivery device and the external computer system device enable enrollment, which can be administered by an independent party trusted by all the stakeholders. According to at least one embodiment of the present invention, enrollment includes a patient swallowing a drug delivery device (possibly a placebo), which securely relays an activation signature to a trusted external computer system (e.g., a local computer, a remote server, a cloud service, etc.). Upon receipt of the activation signature, the trusted computer system generates an encrypted tamper-proof device signature and communicates the device signature to the drug delivery device, where it is stored in a memory device.

According to at least one embodiment of the present invention, the drug delivery device and the external computer system can report status information, for example, of the drug delivery device not opening, etc.

According to at least one embodiment of the present invention, after the drug delivery device is swallowed, all sensor activations are signed using the device signature. Each sensor activation includes the device signature, which is compared with the device signature stored by the external computer system. The external computer system can trigger an action upon a match or a mismatch according to user needs, for example, generating an alarm if the signatures do not match.

According to at least one embodiment of the present invention, the drug delivery device includes an additional medication or substance, such as a contaminant 412 (C) to foil attempts to reverse engineer the medication or a chemical compound to render the medication inert in the case of an attempt to misuse the medication. According to at least one embodiment of the present invention, the contaminant can be released 104 by an actuator under the control of the logic circuit, for example, upon determination of an authorization fail 103.

Recapitulation:

According to at least one embodiment of the present invention, a drug delivery device 200 includes a capsule 201-202, a logic circuit 209 disposed within the capsule, and an actuator 210 connected to the logic circuit and configured to expose an interior of the capsule to an exterior of the capsule upon activation by the logic circuit.

According to an embodiment of the present invention, a method of controlling a drug delivery device comprising a capsule, a logic circuit disposed within the capsule, and an actuator connected to the logic circuit includes sensing a location of the drug delivery device 102, determining entry of the drug delivery device into an intestine using the location 102, communicating an authorization request to an external computer system upon determining entry into the intestine 103, receiving an authorization from the external computer system 104, and activating, by the logic circuit, the actuator to expose an interior of the capsule to an exterior of the capsule upon receipt of the authorization 104.

According to an embodiment of the present invention, a method of controlling a drug delivery device comprising a capsule, a logic circuit disposed within the capsule, and an actuator connected to the logic circuit includes sensing a location of the drug delivery device 102, determining entry of the drug delivery device into an intestine using the location 102, communicating an authorization request to an external computer system upon determining entry into the intestine 103, determining an authorization fail from the external computer system 104, and activating, by the logic circuit, the actuator to render a medication containing with the capsule insert upon receiving the authorization fail upon determination of the authorization fail 104.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

Furthermore, it should be noted that any of the methods described herein can include an additional step of providing a computer system for controlling a drug delivery device comprising a capsule, a logic circuit disposed within the capsule, and an actuator connected to the logic circuit. Further, a computer program product can include a tangible computer-readable recordable storage medium with code adapted to be executed to carry out one or more method steps described herein, including the provision of the system with the distinct software modules.

Figure 6:
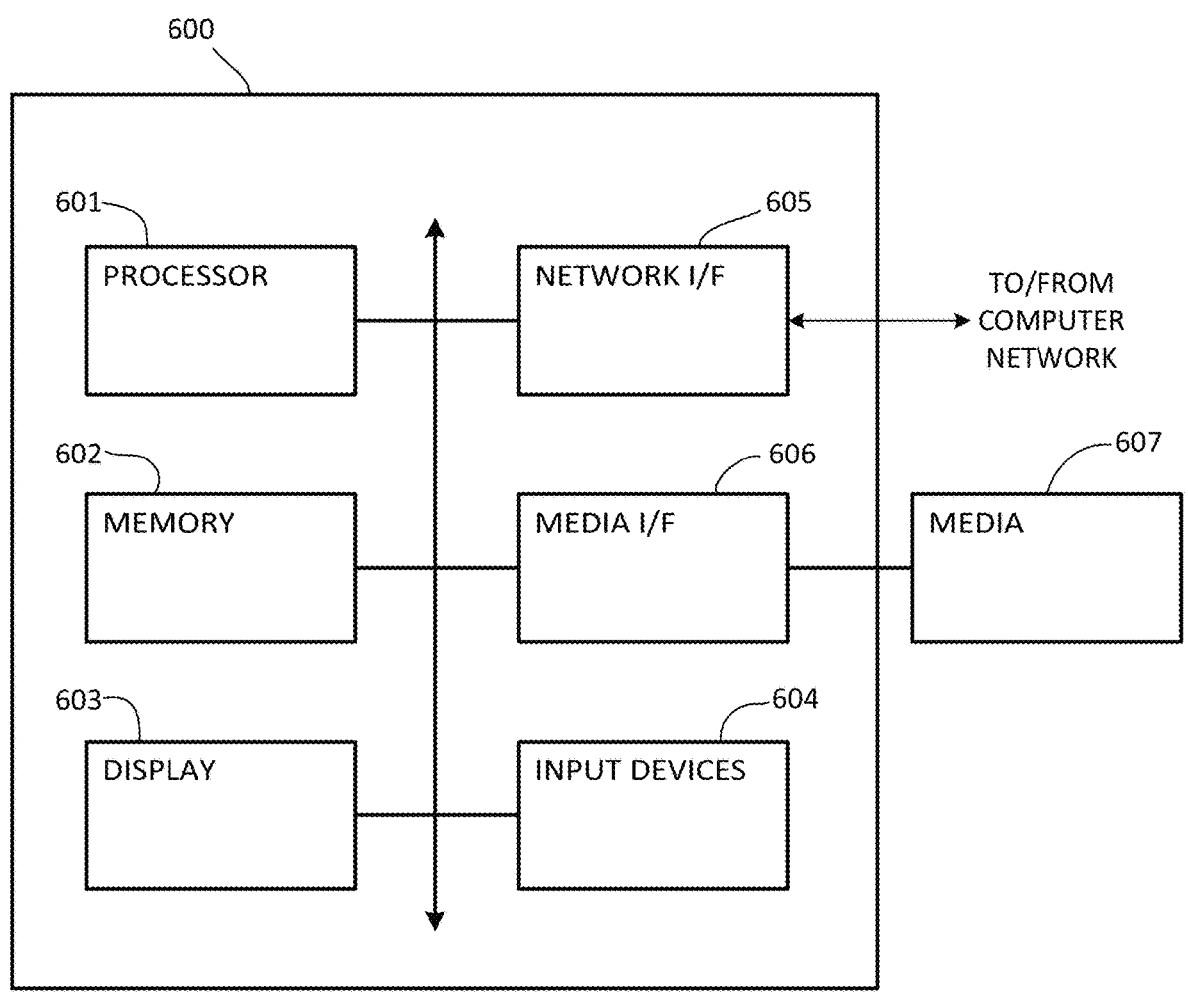
FIG. 6 is a block diagram depicting an exemplary computer system according to an exemplary embodiment of the present invention.

Referring to FIG. 6; FIG. 6 is a block diagram depicting an exemplary computer system 600 configured to function as at least one of an electronics package of a drug delivery device and/or an external computer system according to an embodiment of the present invention. The computer system shown in FIG. 6 includes a processor 601, memory 602, display 603, input device 604 (e.g., keyboard), a network interface (I/F) 605, a media I/F 606, and media 607, such as a signal source, e.g., camera, Hard Drive (HD), external memory device, etc.

In different applications, some of the components shown in FIG. 6 can be omitted. The whole system shown in FIG. 6 is controlled by computer readable instructions, which are generally stored in the media 607. The software can be downloaded from a network (not shown in the figures), stored in the media 607. Alternatively, software downloaded from a network can be loaded into the memory 602 and executed by the processor 601 so as to complete the function determined by the software.

The processor 601 may be configured to perform one or more methodologies described in the present disclosure, illustrative embodiments of which are shown in the above figures and described herein. Embodiments of the present invention can be implemented as a routine that is stored in memory 602 and executed by the processor 601 to process the signal from the media 607. As such, the computer system is a general-purpose computer system that becomes a specific purpose computer system when executing routines of the present disclosure.

Although the computer system described in FIG. 6 can support methods according to the present disclosure, this system is only one example of a computer system. Those skilled of the art should understand that other computer system designs can be used to implement embodiments of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of controlling drug delivery devices, each drug delivery device comprising a capsule, a logic circuit disposed within the capsule, and an actuator connected to the logic circuit, the method comprising:
   sensing a location of a first drug delivery device;
   determining entry of the first drug delivery device into an intestine using the location;
   communicating, by the first drug delivery device, an authorization request seeking permission to activate the actuator to an external computer system upon determining entry of the first drug delivery device into the intestine;
   receiving, by the first drug delivery device, an authorization from the external computer system; and
   activating, by the logic circuit of the first drug delivery device, the actuator of the first drug delivery device to expose an interior of the capsule of the first drug delivery device to an exterior of the capsule in response to receipt of the authorization.

2. The method of claim 1, further comprising communicating a successful activation of the actuator of the first drug delivery device to the external computer system.

3. The method of claim 1, further comprising logging, by the external computer system, the authorization of the activation of the actuator of the first drug delivery device to the external computer system.

4. The method of claim 1, further comprising:
sensing a location of a second drug delivery device;
determining entry of the second drug delivery device into the intestine using the location;
communicating, by the second drug delivery device, a second authorization request to the external computer system upon determining entry of the second drug delivery device into the intestine;
receiving, by the second drug delivery device, an authorization fail from the external computer system; and
activating, by the logic circuit of the second drug delivery device, the actuator of the second drug delivery device to render a medication contained within the capsule of the second drug delivery device inert upon receiving the authorization fail.

5. The method of claim 4, further comprising logging, by the external computer system, the authorization fail.

\* \* \* \* \*